(12) United States Patent
Kanagaraj et al.

(10) Patent No.: US 8,470,809 B2
(45) Date of Patent: Jun. 25, 2013

(54) CRYSTALLINE SODIUM SALT OF CEPHALOSPORIN ANTIBIOTIC

(75) Inventors: Sureshkumar Kanagaraj, Chennai (IN); Sivakumar Balasubramanian, Chennai (IN); Senthilkumar Udayampalayam Palanisamy, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 309 days.

(21) Appl. No.: 12/903,751

(22) Filed: Oct. 13, 2010

(65) Prior Publication Data

US 2011/0059933 A1 Mar. 10, 2011

Related U.S. Application Data

(63) Continuation-in-part of application No. 12/089,821, filed as application No. PCT/IB2006/002842 on Oct. 12, 2006, now Pat. No. 8,212,024.

(30) Foreign Application Priority Data

Oct. 12, 2005 (IN) ............................ 1462/CHE/2005
Nov. 18, 2005 (IN) ............................ 1680/CHE/2005

(51) Int. Cl.
*A61K 31/546* (2006.01)
(52) U.S. Cl.
USPC ........................................ 514/206; 540/227
(58) Field of Classification Search
USPC ....................................................... 514/206
See application file for complete search history.

(56) References Cited

U.S. PATENT DOCUMENTS

| | | | |
|---|---|---|---|
| 4,464,367 A | 8/1984 | Labeeuw et al. | |
| 4,902,683 A | 2/1990 | Amin et al. | |
| 4,937,330 A | 6/1990 | Sacks et al. | |
| 5,079,007 A | 1/1992 | Putnam | |
| 5,721,359 A | 2/1998 | Dunn et al. | |
| 6,458,949 B1 * | 10/2002 | Handa et al. | 540/226 |
| 6,555,680 B1 * | 4/2003 | Deshpande et al. | 540/227 |
| 6,610,845 B1 * | 8/2003 | Deshpande et al. | 540/215 |
| 6,803,461 B2 * | 10/2004 | Deshpande et al. | 540/226 |
| 7,071,329 B2 * | 7/2006 | Monguzzi et al. | 540/226 |
| 7,345,169 B2 * | 3/2008 | Senthilkumar et al. | 544/227 |
| 7,511,135 B2 * | 3/2009 | Tyagi et al. | 540/227 |
| 8,212,024 B2 * | 7/2012 | Senthilkumar et al. | 540/227 |
| 2002/0028931 A1 | 3/2002 | Dandala et al. | |
| 2002/0082248 A1 * | 6/2002 | Berger et al. | 514/206 |
| 2003/0065168 A1 | 4/2003 | Deshpande et al. | |
| 2004/0132996 A1 * | 7/2004 | Tyagi et al. | 540/227 |
| 2005/0119244 A1 * | 6/2005 | Monguzzi et al. | 514/202 |
| 2006/0094872 A1 * | 5/2006 | Senthilkumar et al. | 540/217 |
| 2006/0135761 A1 * | 6/2006 | Datta et al. | 540/222 |
| 2008/0207912 A1 * | 8/2008 | Tyagi et al. | 548/195 |
| 2011/0136777 A1 * | 6/2011 | Udayampalayam Palanisamy et al. | 514/206 |

FOREIGN PATENT DOCUMENTS

| | | | |
|---|---|---|---|
| IN | 2003MU01140 | * | 10/2003 |
| IN | 2005CH01773 | * | 12/2005 |
| WO | WO 2007/042417 A1 | | 4/2007 |
| WO | WO 2010/020871 A2 | | 2/2010 |

OTHER PUBLICATIONS

International Search Report issued in International Application No. PCT/IB2006/002842 on Dec. 14, 2006.
International Preliminary Report on Patentability issued in International Application No. PCT/IB2006/002842 on Apr. 15, 2008.

* cited by examiner

*Primary Examiner* — Mark Berch
(74) *Attorney, Agent, or Firm* — Oliff & Berridge, PLC

(57) ABSTRACT

The present invention relates to novel polymorph of Ceftiofur sodium as a crystalline product. The present invention also provides a process for the preparation of novel polymorphs of crystalline Ceftiofur sodium of formula (I).

(I)

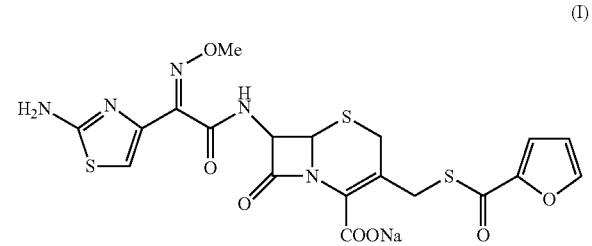

9 Claims, 2 Drawing Sheets

CRYSTALLINE SODIUM SALT OF CEPHALOSPORIN ANTIBIOTIC

The present application is a continuation in part of U.S. application Ser. No. 12/089,821 filed on Oct. 4, 2008; which is a national phase application of PCT/IB 2006/002842

FIELD OF THE INVENTION

The present invention relates to novel polymorph of Ceftiofur sodium as a crystalline product. This invention further relates to a process for the preparation of novel polymorph of Ceftiofur sodium.

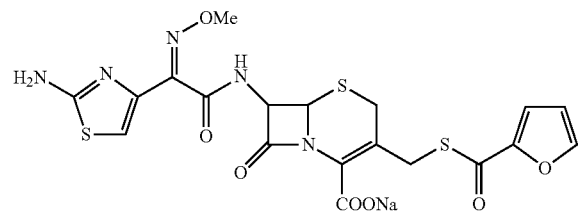

(I)

BACKGROUND OF THE INVENTION

Ceftiofur, a semisynthetic cephalosporin, is a broad-spectrum antibiotic against both Gram-positive and Gram-negative bacteria including beta-lactamase-producing bacterial strains and anaerobes. Its antibacterial activity results from the inhibition of mucopeptide synthesis in the cell wall in a similar fashion to other cephalosporins. Ceftiofur is used in the treatment of respiratory infections in cattle and pigs. The chemical designation is 7-[[(2-amino-4-thiazolyl)(methoxyimino)acetyl]amino]-3-[[2-furanylcarbonyl)thio]methyl]-8-oxo-5-thia-1-azabicyclo[4.2.0]oct-2-ene-2-carboxylic acid. The sodium and hydrochloride salts are administered intramuscularly and intravenously.

Ceftiofur is first disclosed in U.S. Pat. No. 4,464,367, which also discloses a process for preparing Ceftiofur and its sodium salt.

U.S. Pat. No. 4,902,683 claims crystalline hydrochloride salt of Ceftiofur. According to this patent the conventional free acid and its sodium salt are unstable and are obtained as amorphous in nature.

U.S. Pat. No. 5,721,359 claims crystalline Ceftiofur free acid and process for the preparation of same.

U.S. Pat. No. 4,937,330 claims a process for the preparation of Ceftiofur sodium. According to this patent Ceftiofur sodium is isolated from aqueous tetrahydrofuran as a unique solid phase characterized by birefringent lath- and rod-shaped particles. Moreover further treatment with a dry organic solvent (e.g., acetone or ethanol) produces solvent-free amorphous Ceftiofur sodium upon drying.

Hence all the prior art literature reported so far provide amorphous Ceftiofur sodium, and owing to the amorphous nature, the conventional Ceftiofur sodium is less stable. Further, owing to the amorphous nature, purification is very difficult, and hence not preferable in large scale preparation.

In our PCT publication WO 2007/042917 (Indian Application No. 1462/CHE/2005) a novel polymorph of crystalline Ceftiofur Sodium having moisture content in the range of 7.0 to 11.0% is provided and is named as Form D.

In our PCT publication WO 2010/020871 (Indian Application No. 2047/CHE/2008) a novel polymorph of anhydrous crystalline Ceftiofur Sodium (Form A) and Ceftiofur sodium monohydrate (Form M) having moisture content in the range of 3.0-4.5% are provided.

In our continued research we have identified novel crystalline form of Ceftiofur sodium having moisture content in the range of 4.6 to 7.0% and having a distinct PXRD pattern, which is having good stability over conventional amorphous product.

OBJECTIVES OF THE INVENTION

The primary objective of the present invention is to provide a novel crystalline polymorph of Ceftiofur sodium of formula (I) having moisture content in the range of 4.6-7.0% hereinafter called as Form O of Ceftiofur sodium, which is having good stability than conventional amorphous Ceftiofur sodium.

Yet another objective of the present invention is to provide a pharmaceutical composition containing crystalline polymorph of Form O of Ceftiofur sodium.

Still another objective of the invention is to provide a process for the preparation of crystalline polymorph of Form O of Ceftiofur sodium.

SUMMARY OF THE INVENTION

Accordingly, the present invention provides novel crystalline polymorph of Ceftiofur sodium (Form O) of formula (I), having moisture content in the range of 4.6-7.0% and having substantially the same X-ray diffractogram as set out in FIG. 1.

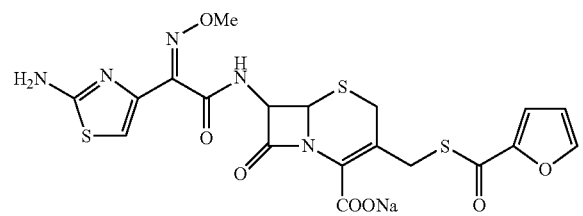

(I)

The present invention also provides a process for the preparation of Form O of Ceftiofur sodium which comprises controlled drying of hydrated polymorph of Ceftiofur sodium (Form D) at a temperature in the range of 35 to 50° C. & under vacuum till the moisture content reaches 4.6 to 7.0%.

The PXRD is measured using Diffractometer of following features:

| | |
|---|---|
| Make | BRUKER AXS |
| Model | D8 ADVANCE |
| Data handling system | EVA 12.0.0.0. |
| ANODE | COPPER |
| RADIATION | COPPER K alpha-1 |
| WAVELENGTH | 1.5406 A° |
| CURRENT &VOLTAGE | 40 kV 30 mA |

DETAILED DESCRIPTION OF THE INVENTION

In an embodiment of the present invention, novel crystalline polymorph of Ceftiofur sodium (Form O) of formula (I) having moisture content 4.6-7.0% is characterized by X-ray powder diffraction peaks (±0.2° 2θ) as shown in the following table-1:

TABLE 1

| 2-Theta ° | I % |
|---|---|
| 3.70 | 12.9 |
| 4.89 | 10.6 |
| 6.43 | 34.7 |
| 7.44 | 38.9 |
| 9.86 | 60.1 |
| 12.66 | 12.1 |
| 14.60 | 100.0 |
| 14.85 | 33.9 |
| 15.21 | 19.8 |
| 18.07 | 28.9 |
| 18.47 | 16.4 |
| 19.35 | 16.6 |
| 19.96 | 21.2 |
| 20.89 | 29.3 |
| 21.08 | 22.8 |
| 21.30 | 28.3 |
| 21.89 | 56.1 |
| 22.41 | 29.1 |
| 22.83 | 10.7 |
| 23.14 | 9.1 |
| 24.06 | 16.2 |
| 24.67 | 23.2 |
| 25.02 | 14.5 |
| 25.54 | 33.5 |
| 25.98 | 13.7 |
| 26.51 | 11.0 |
| 26.71 | 10.0 |
| 27.53 | 22.1 |
| 27.81 | 26.2 |
| 28.80 | 9.5 |
| 29.55 | 9.6 |
| 29.95 | 9.5 |
| 30.21 | 15.3 |
| 31.63 | 11.3 |
| 32.78 | 22.5 |
| 35.59 | 13.8 |
| 35.90 | 9.6 |
| 38.74 | 10.1 |
| 39.59 | 9.0 |

Figure 2:
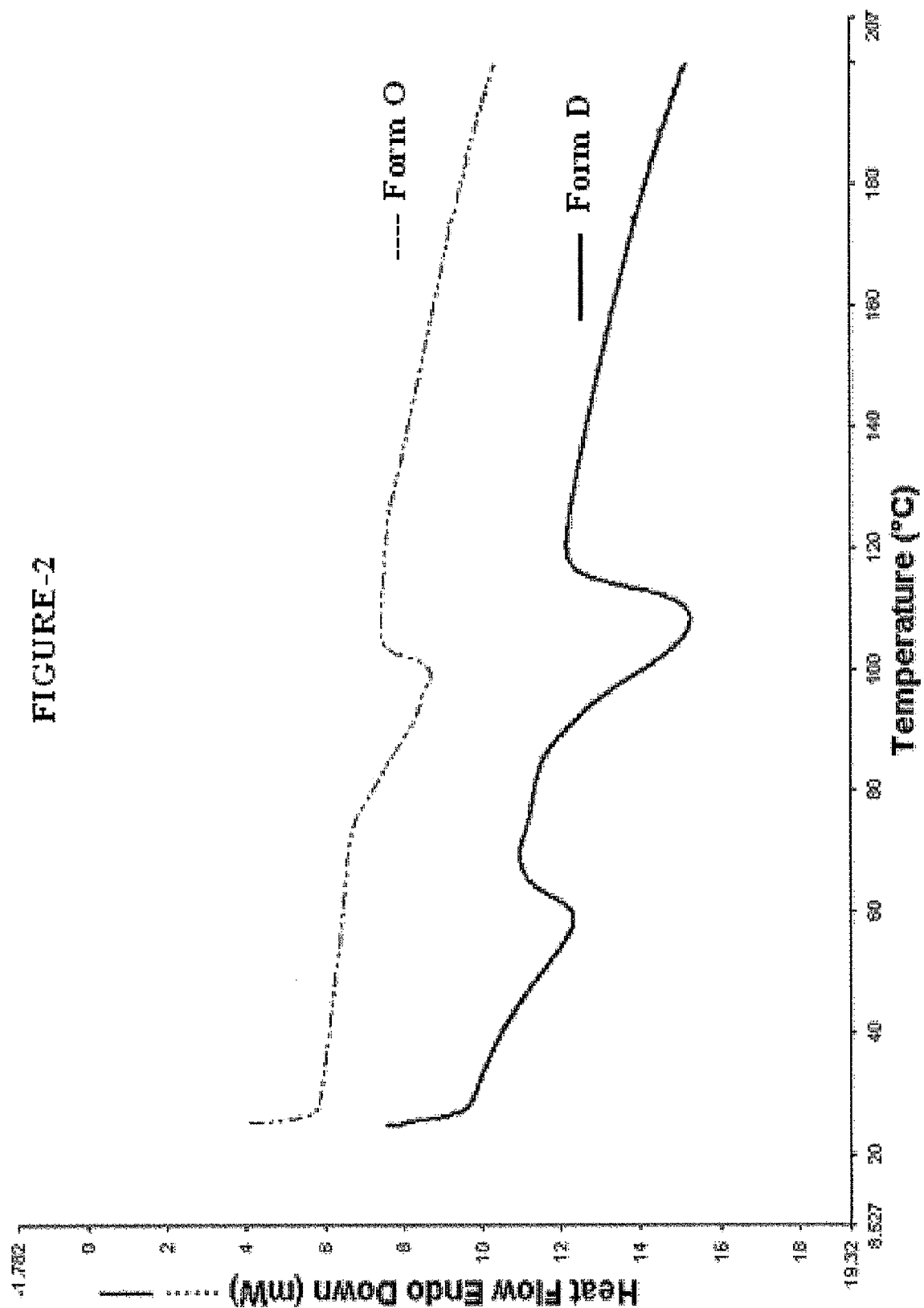
FIG. 2: DSC comparison of Form O of present invention and Form D (as provided in WO 2010/020871).

In one more embodiment of the present invention, the crystalline polymorph of Ceftiofur sodium (Form O) of formula (I) having moisture content 4.6-7.0% is obtained by controlled drying of hydrated Ceftiofur sodium (Form D) under vacuum at a temperature in the range of 35 to 50° C. for 1-3 hours till the moisture content reaches 4.6 to 7.0%. The obtained Ceftiofur Form O is handled for the further operation preferably under dehumidified area. The moisture content of Ceftiofur sodium is measured by using Karl-Fisher technique. The Ceftiofur sodium obtained according to the present invention is stored under inert condition, for example packed under nitrogen atmosphere. FIG. 2, clearly indicates the DSC of Form O of Ceftiofur sodium obtained by the process of the present invention is different from the Form D.

The starting material of the present invention can be prepared or obtained by utilizing the process available in the prior art (for example prepared by utilizing the technique available in WO 2007/042917).

Crystalline materials are preferred in most pharmaceutical applications since crystalline forms have better flow properties, and are thermodynamically more stable than amorphous forms of the same substance. This thermodynamic stability is reflected in the lower solubility and improved physical stability of the crystalline form. The regular packing of the molecules in the crystalline solid denies the incorporation of chemical impurities. Hence crystalline materials generally possess higher chemical purity than their amorphous counterparts.

In one more embodiment of the present invention, the Ceftiofur sodium obtained according to the present invention having good stability over conventional amorphous Ceftiofur sodium and also has less residual solvent over the amorphous sample prepared by prior art.

The following table provides a comparison of physical characteristics of amorphous and crystalline Ceftiofur Sodium (Form O). From this table, it is evident that the crystalline Ceftiofur Sodium Form O has better physical characteristics than amorphous material.

TABLE 2

Comparison between Amorphous and Crystalline Ceftiofur sodium (Form O)

| No | Test | Amorphous | Crystalline (Form O) |
|---|---|---|---|
| 1 | Description | Pale yellow powder | Off-white powder |
| 2 | Tapped Bulk density | <0.50 g/cc | >0.80 g/cc |
| 3 | Reconstituted solution color | Pale yellow colour solution | Colourless solution |
| 4 | Total Related substances | >4.00% | <0.25% |

The crystalline Ceftiofur Sodium (Form O) prepared according to this invention has good stability for longer period and purity because of which the potency of crystalline Ceftiofur sodium is maintained over a long shelf life period unlike the amorphous Ceftiofur Sodium.

Form O of Ceftiofur sodium obtained according to the present invention may be used for the same indications as Ceftiofur sodium provided by a prior art process or Ceftiofur sodium currently on the market. Form O of Ceftiofur sodium according to this invention useful as the active antibiotic drug compound in pharmaceutical dosage forms for treating valuable mammalian animals and humans to treat bacterial infections in that valuable animal or human, and more particularly useful as a veterinary antibiotic drug to treat valuable animals such as cattle, swine, horses, sheep, goats, dogs and cats to fight the effects of bacterial infections caused by susceptible organisms, such as *Pasturella hemolitica, Pasturella multiocida, Salmonella typhimurium, Salmonella choleraeasuis, Actinbacillus plearopneumoniae, Streptococcus suis, Haemophilus somnus, E. coli, Staphylococcus aureus* and the like, some of which are commonly associated with diseases in animals, such as bovine respiratory disease and swine respiratory disease.

In one more embodiment of the present invention the Form O of Ceftiofur sodium prepared according to the present invention may be administered in any conventional dosage form in any conventional manner, routes of administration and dosage form are exemplified in various prior art related to Ceftiofur and also exemplified in U.S. Pat. No. 4,464,367; U.S. Pat. No. 4,902,683, U.S. Pat. No. 5,079,007, and U.S. Pat. No. 5,721,359.

Apart from the conventional formulation that are described for the Ceftiofur sodium formulation may also contain chelating agent like ethylenediamine tetraacetic acid (EDTA) or a buffer like sodium citrate along with or with out conventional excipient. The pharmaceutical composition may also contain amorphous Ceftiofur sodium, Form D, Form M, Form A of Ceftiofur sodium along with crystalline Ceftiofur sodium (Form O). Accordingly the present invention provides a pharmaceutical composition comprising one or more of Ceftiofur sodium selected from Form O, amorphous form, Form D, Form M, and Form A. The pharmaceutical composition may also contain conventional buffer and/or base.

Many other beneficial results can be obtained by applying the disclosed invention in a different manner or by modifying the invention with the scope of disclosure.

The present invention is provided by the examples below, which are provided by way of illustration only and should not be considered to limit the scope of the invention.

Example 1

Preparation of Ceftiofur Sodium Crystalline

Form O

Figure 1:
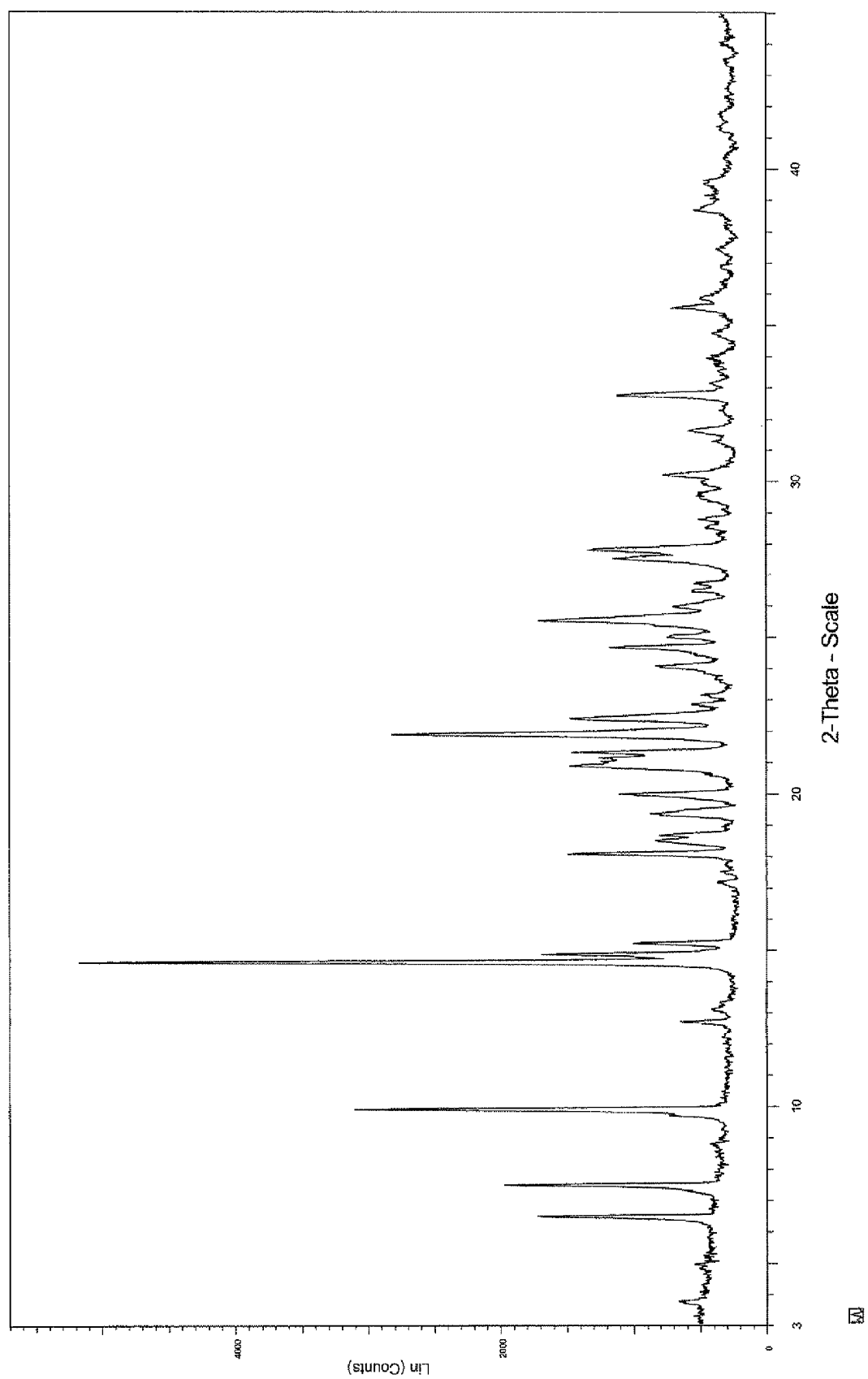
FIG. 1: Powder XRD pattern of novel crystalline form of Ceftiofur sodium of formula (I) (Form O).

The crystalline Ceftiofur sodium having moisture content about 7.0-11% (prepared according to the process provided in WO 2007/042917) was dried under vacuum at 45° C. for 1 hour.
The powder XRD pattern substantially same as depicted in FIG-1 & Table-2
Purity: 99.77%. Moisture content: 6.43%.
Advantages:
  Enhanced stability even at elevated temperature.
  High purity.
  Good Colour, flow-properties and high bulk density.
  Suitable dissolubility & improved shelf life.

Example 2

Preparation of Buffered Ceftiofur Sodium

Form O (or Form D or both) of crystalline sterile Ceftiofur sodium was blended with lyophilized mixture of potassium dihydrogen orthophosphate and sodium hydroxide (prepared according to the process provided in 2023/CHE/2007) till to get uniform pH.

We claim:

1. A crystalline polymorph of Ceftiofur sodium of formula (I)

having an X-ray diffraction pattern that comprises 2θ values (Cu K alpha-1λ=1.5406 A°.) of 3.70, 4.89, 6.43, 7.44, 9.86, 12.66, 14.60, 14.85, 15.21, 18.07, 18.47, 19.35, 19.96, 20.89, 21.08, 21.30, 21.89, 22.41, 22.83, 23.14, 24.06, 24.67, 25.02, 25.54, 25.98, 26.51, 26.71, 27.53, 27.81, 28.80, 29.55, 29.95, 30.21, 31.63, 32.78, 35.59, 35.90, 38.74, 39.59 (±0.20).

2. The crystalline polymorph of Ceftiofur sodium of formula (I) as claimed in claim 1 having an X-ray diffractogram as set out in FIG. 1.

3. The crystalline polymorph of Ceftiofur sodium as claimed in claim 1 having the moisture content in the range of 4.6 to 7.0%.

4. The crystalline polymorph of Ceftiofur sodium as claimed in claim 1 having the moisture content in the range of 5.5 to 7.0%.

5. A process for the preparation of the crystalline polymorph of Ceftiofur sodium of formula (I) as claimed in claim 1 comprising drying the Ceftiofur sodium (Form D) having a moisture content in the range of 7.0 to 11.0% at a temperature in the range of 35 to 50° C. under vacuum until the moisture content reaches 4.6 to 7.0%.

6. The process as claimed in claim 5, wherein the drying is performed under vacuum for 1-3 hours.

7. A pharmaceutical composition comprising the crystalline polymorph of Ceftiofur sodium of claim 1 and a buffer.

8. A Physical admixture of the crystalline polymorph of Ceftiofur sodium as claimed in claim 1, with lyophilized composition of potassium dihydrogen orthophosphate and sodium hydroxide.

9. A pharmaceutical composition comprising a mixture of the crystalline polymorph of Ceftiofur sodium as claimed in claim 1 with amorphous Ceftiofur sodium.

* * * * *